United States Patent [19]

Takaya et al.

[11] Patent Number: 4,927,818

[45] Date of Patent: May 22, 1990

[54] CEPHEM COMPOUNDS AND PROCESSES FOR PREPARATION THEREOF

[75] Inventors: Takao Takaya; Kazuo Sakane; Kenzi Miyai, all of Kawanishi; Kohji Kawabata, Osaka, all of Japan

[73] Assignee: Fujisawa Pharmaceutical Co., Ltd., Osaka, Japan

[21] Appl. No.: 90,345

[22] Filed: Aug. 28, 1987

[30] Foreign Application Priority Data

| Sep. 22, 1986 | [GB] | United Kingdom | 8622766 |
| Nov. 24, 1986 | [GB] | United Kingdom | 8628061 |
| Mar. 4, 1987 | [GB] | United Kingdom | 8705072 |
| May 18, 1987 | [GB] | United Kingdom | 8711653 |
| Jul. 13, 1987 | [GB] | United Kingdom | 8716437 |

[51] Int. Cl.$^5$ ................. A61K 31/545; C07D 501/46
[52] U.S. Cl. ..................................... 514/202; 540/222
[58] Field of Search ........................ 514/202; 540/222

[56] References Cited

U.S. PATENT DOCUMENTS

| 4,268,509 | 5/1981 | Teraji et al. | 540/227 |
| 4,332,800 | 6/1982 | Teraji et al. | 540/225 |
| 4,425,340 | 1/1984 | Teraji et al. | 540/225 |
| 4,457,928 | 7/1984 | Teraji et al. | 540/225 |
| 4,464,368 | 8/1984 | O'Callaghan | 540/222 |
| 4,495,182 | 1/1985 | Teraji et al. | 540/225 |
| 4,521,413 | 6/1985 | Teraji et al. | 540/225 |
| 4,563,449 | 1/1986 | Teraji et al. | 540/225 |
| 4,665,065 | 5/1987 | Miyake | 540/222 |

FOREIGN PATENT DOCUMENTS

| 47977 | 3/1982 | European Pat. Off. | 540/222 |
| 0062321 | 10/1982 | European Pat. Off. | |
| 0223246 | 5/1987 | European Pat. Off. | |
| 3419012 | 10/1985 | Fed. Rep. of Germany | 540/222 |
| 61-286389 | 12/1986 | Japan | 540/222 |
| 8106321 | 7/1982 | South Africa | |

OTHER PUBLICATIONS

Burger, A., *Medicinal Chemistry*, 2nd ed, (1960: Interscience Publishers, Inc.; New York), p. 42.

*Primary Examiner*—Donald G. Daus
*Attorney, Agent, or Firm*—Oblon, Spivak, McClelland, Maier & Neustadt

[57] ABSTRACT

7 β-[2-5 amino-1, 2, 4 thiadiazol-3yl) 2(carboxy lower alkyleneoxyimino) acetamido]-3-(3-amino-2-alkyl-1-pyrazolio) methyl 3 cephem 4 carboxylates are prepared. They are antibiotics.

9 Claims, No Drawings

CEPHEM COMPOUNDS AND PROCESSES FOR PREPARATION THEREOF

The present invention relates to new cephem compounds and pharmaceutically acceptable salts thereof. More particularly, it relates to new cephem compounds and pharmaceutically acceptable salts thereof, which have antimicrobial activities, to process for preparation thereof, to pharmaceutical composition comprising the same, and to a method for treating infectious diseases in human being and animals.

Accordingly, one object of the present invention is to provide the cephem compounds and pharmaceutically acceptable salts thereof, which are highly active against a number of pathogenic microorganisms.

Another object of the present invention is to provide processes for the preparation of the cephem compounds and salts thereof.

A further object of the present invention is to provide pharmaceutical compositions comprising, as an active ingredient, said cephem compounds or their pharmaceutically acceptable salts.

Still further object of the present invention is to provide a method for treating infectious diseases caused by pathogenic microorganisms, which comprises administering said cephem compounds to infected human being or animals.

The object cephem compounds of the present invention are novel and can be represented by the following general formula [I]:

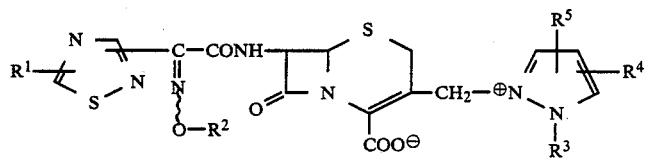

wherein
$R^1$ and $R^4$ are each amino or a protected amino group,
$R^2$ is carboxy(lower)alkyl or a protected carboxy(lower)alkyl,
$R^3$ is lower alkyl, hydroxy(lower)alkyl or a protected hydroxy(lower)alkyl and
$R^5$ is hydrogen or lower alkyl.

As to the object compounds [I], the following points are to be noted.

That is, the object compounds [I] include syn isomer, anti isomer and a mixture thereof. Syn isomer means one geometrical isomer having the partial structure represented by the following formula:

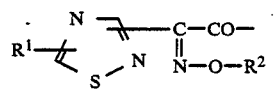

(wherein $R^1$ and $R^2$ are each as defined above) and anti isomer means the other geometrical isomer having the partial structure represented by the following formula:

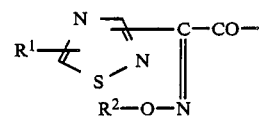

(wherein $R^1$ and $R^2$ are each as defined above), and all of such geometrical isomers and mixture thereof are included within the scope of this invention.

In the present specification and claim, the partial structure of these geometrical isomers and mixture thereof are represented for convenient sake by the following formula:

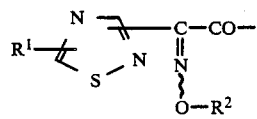

(wherein $R^1$ and $R^2$ are each as defined above).

Another point to be noted is that the pyrazolio moiety of the compounds [I] can also exist in the tautomeric form, and such tautomeric equilibrium can be represented by the following schemes.

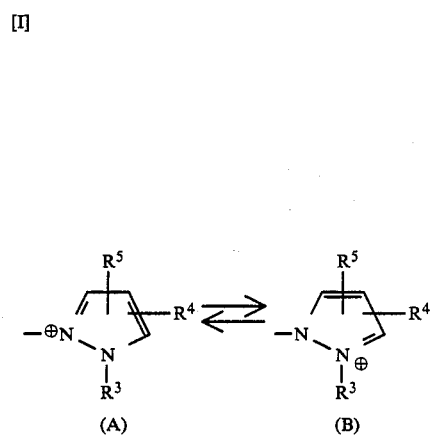

(wherein $R^3$, $R^4$ and $R^5$ are each as defined above).

Both of the above tautomeric isomers are included within the scope of the present invention, and in the present specification and claim, however, the object compounds [I] are represented for the convenient sake by one expression of the pyrazolio group of the formula (A).

The cephem compounds [I] of the present invention can be prepared by processes as illustrated in the followings.

Process 1

-continued

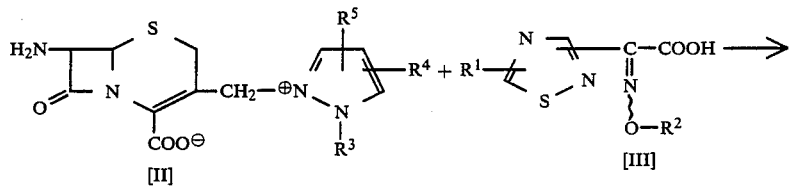

[II]
or its reactive derivative at the
amino group or a salt thereof

[III]
or its reactive derivative at the
carboxy group or a salt thereof

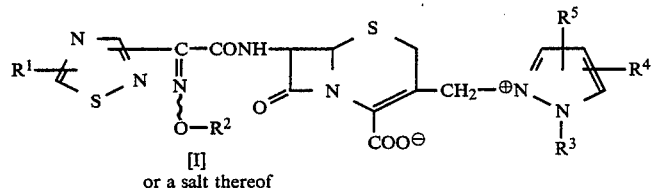

[I]
or a salt thereof

Process 2

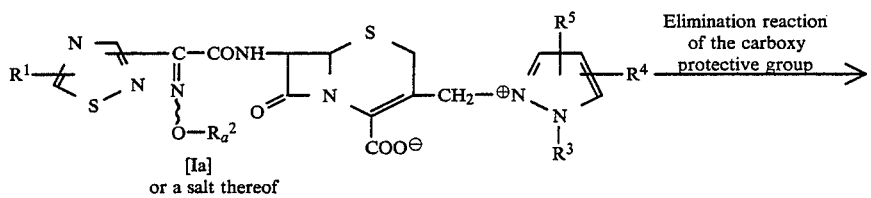

[Ia]
or a salt thereof

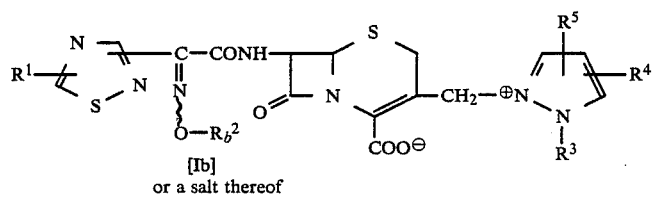

[Ib]
or a salt thereof

Process 3

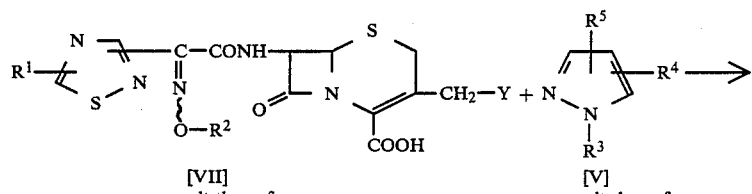

[VII]
or a salt thereof

[V]
or a salt thereof

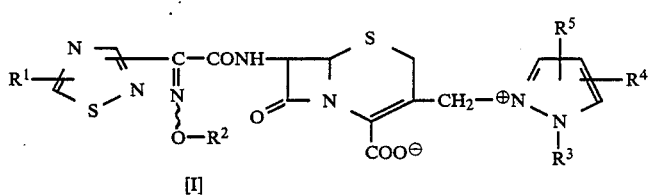

[I]
or a salt thereof wherein
$R^1$, $R^2$, $R^3$, $R^4$ and $R^5$ are each as defined above,
$R_a^2$ is a protected carboxy(lower)alkyl,
$R_{bhu}^2$ is carboxy(lower)alkyl, and
Y is a leaving group.

In the above and subsequent descriptions of this specification, suitable examples of the various definitions are explained in detail as follows :

The term "lower" is intended to mean 1 to 6 carbon atom(s), unless otherwise indicated.

Suitable "protective group" in the "protected amino group" may be lower alkanoyl [e.g. formyl, acetyl, propionyl, hexanoyl, pivaloyl, etc.], mono(or di or tri)-halo(lower)alkanoyl [e.g. chloroacetyl, trifluoroacetyl, etc.], lower alkoxycarbonyl [e.g. methoxycarbonyl, ethoxycarbonyl, tert-butoxycarbonyl, tert-pentyloxycarbonyl, hexyloxycarbonyl, etc.], carbamoyl, aroyl [e.g. benzoyl, toluoyl, naphthoyl, etc.], ar(lower)alkanoyl [e.g. phenylacetyl, phenylpropionyl, etc.], aryloxycarbonyl [e.g. phenoxycarbonyl, naphthyloxycarbonyl, etc.], aryloxy(lower)alkanoyl [e.g. phenoxyacetyl, phenoxypropionyl, etc.], arylglyoxyloyl [e.g. phenylglyoxyloyl, naphthylglyoxyloyl, etc.], ar(lower)alkoxycarbonyl which may have suitable substituent(s) [e.g. benzyloxycarbonyl, phenethyloxycarbonyl, p-nitrobenzyloxycarbonyl, etc.], substituted or unsubstituted ar(lower)alkylidene [e.g. benzylidene, hydroxybenzylidene, etc.], ar(lower)alkyl such as mono or di or triphenyl(lower)alkyl [e.g. benzyl, phenethyl, benzhydryl, trityl, etc.], or the like, in which the preferred one may be lower alkanoyl or carbamoyl and the more preferred one may be $C_1$-$C_4$alkanoyl or carbamoyl.

Suitable "lower alkyl" and "lower alkyl moieties" in the "caboxy(lower)alkyl", "protected carboxy(lower)alkyl", "hydroxy(lower)alkyl" and "protected hydroxy-(lower)alkyl" may be a straight or branched one such as methyl, ethyl, propyl, isopropyl, butyl, isobutyl, tert-butyl, pentyl, hexyl, or the like, in which the preferred one may be $C_1$-$C_4$alkyl.

Suitable "protected carboxy" in the "protected carboxy(lower)alkyl" may be an esterified carboxy group, or the like, and concrete examples of the ester moiety in said esterified carboxy group may be the ones such as lower alkyl ester [e.g. methyl ester, ethyl ester, propyl ester, isopropyl ester, butyl ester, isobutyl ester, tert-butyl ester, pentyl ester, hexyl ester, 1-cyclopropylethyl ester, etc.] which may have suitable substituent(s), for example, lower alkanoyloxy(lower)alkyl ester [e.g. acetoxymethyl ester, propionyloxymethyl ester, butyryloxymethyl ester, valeryloxymethyl ester, pivaloyloxymethyl ester, 1-acetoxyethyl ester, 1-propionyloxyethyl ester, pivaloyloxymethyl ester, 2-propionyloxyethyl ester, hexanoyloxymethyl ester, etc.], lower alkanesulfonyl(lower)alkyl ester [e.g. 2-mesylethyl ester, etc.] or mono(or di or tri)halo(lower)alkyl ester [e.g. 2-iodoethyl ester, 2,2,2-trichloroethyl ester, etc.]; lower alkenyl ester [e.g. vinyl ester, allyl ester, etc.]; lower alkynyl ester [e.g. ethynyl ester, propynyl ester, etc.]; ar(lower)alkyl ester which may have suitable substituent(s) [e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-tert-butylbenzyl ester, etc.]; aryl ester which may have suitable substituent(s) [e.g. phenyl ester, 4-chlorophenyl ester, tolyl ester, 4-tert-butylphenyl ester, xylyl ester, mesityl ester, cumenyl ester, etc.]; or the like.

Suitable "protected hydroxy" in the "protected hydroxy(lower)alkyl" may be acyloxy group or the like. Suitable "acyl moiety" in the "acyloxy" may be lower alkanoyl [e.g. formyl, acetyl, propionyl, hexanoyl, pivaloyl, etc., mono(or di or tri)halo(lower)alkanoyl [e.g. chloroacetyl, trifluoroacetyl, etc.], lower alkoxycarbonyl [e.g. methoxycarbonyl, ethoxycarbonyl, tert-butoxycarbonyl, tert-pentyloxycarbonyl, hexyloxycarbonyl, etc.]or the like.

Suitable "leaving group" may be halogen [e.g. chlorine, bromine, iodine, etc.], acyloxy such as sulfonyloxy [e.g. benzenesulfonyloxy, tosyloxy, mesyloxy, etc.], lower alkanoyloxy [e.g. acetyloxy, propionyloxy, etc.], or the like.

Suitable pharmaceutically acceptable salts of the object compounds [I] are conventional non-toxic salts and include a metal salt such as an alkali metal salt [e.g. sodium salt, potassium salt, etc.] and an alkaline earth metal salt [e.g. calcium salt, magnesium salt, etc.], an ammonium salt, an organic base salt [e.g. trimethylamine salt, triethylamine salt, pyridine salt, picoline salt, dicyclohexylamine salt, N,N'-dibenzylethylenediamine salt, etc.], an organic acid salt [e.g. formate, acetate, trifluoroacetate, maleate, tartrate, methanesulfonate, benzenesulfonate, toluenesulfonate, etc.], an inorganic acid salt [e.g. hydrochloride, hydrobromide, sulfate, phosphate, etc.], a salt with an amino acid [e.g. arginine salt, aspartic acid salt, glutamic acid salt, etc.], and the like.

Preferred embodiments of the object compound [I] are as follows.

Preferred embodiment of $R^1$ is amino, $R^2$ is carboxy(lower)alkyl [more preferably carboxy-($C_1$-$C_4$)alkyl, most preferably carboxymethyl or 1-carboxy-1-methylethyl] or an esterfied carboxy(lower)-alkyl [more preferably lower alkoxycarbonyl(lower)-alkyl, most preferably lower alkoxycarbonyl($C_1$-$C_4$)-alkyl], $R^3$ is lower alkyl [more preferably ($C_1$-$C_4$)alkyl, most preferably methyl] or hydroxy(lower)alkyl [more preferably hydroxy($C_1$-$C_4$)alkyl, most preferably hydroxyethyl], $R^4$ is amino, lower alkanoylamino or ureido, $R^5$ is hydrogen or lower alkyl [more preferably ($C_1$-$C_4$)-alkyl, most preferably methyl].

The processes for preparing the object compounds of the present invention are explained in detail in the following.

Process 1

The object compound [I] or a salt thereof can be prepared by reacting a compound [II] or its reactive derivative at the amino group or a salt thereof with a compound [III] or its reactive derivative at the carboxy group or a salt thereof.

Suitable reactive derivative at the amino group of the compound [II] may include Schiff's base type imino or its tautomeric enamine type isomer formed by the reaction of the compound [II] with a carbonyl compound such as aldehyde, ketone or the like; a silyl derivative formed by the reaction of the compound [II] with a silyl compound such as bis(trimethylsilyl)acetamide, mono(-trimethylsilyl)acetamide [e.g. N-(trimethylsilyl)acetamide], bis(trimethylsilyl)urea or the like; a derivative formed by reaction of the compound [II] with phosphorus trichloride or phosgene, and the like.

Suitable lsalts of the compound [II] and its reactive derivative can be referred to the ones as exemplified for the compound [I].

Suitable reactive derivative at the carboxy group of the compound [III] may include an acid halide, an acid anhydride, an activated amide, an activated ester, and the like. Suitable examples of the reactive derivatives may be an acid chloride; an acid azide; a mixed acid anhydride with an acid such as substituted phosphoric acid [e.g. dialkylphosphoric acid, phenylphosphoric acid, diphenylphosphoric acid dibenzylphosphoric acid, halogenated phosphoric acid, etc.], dialkylphosphorous acid, sulfurous acid, thiosulfuric acid, sulfuric acid, sulfonic acid [e.g. methanesulfonic acid, etc.], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 4-substituted imidazole, dimethylpyrazole, triazole or tetrazole; or an activated ester [e.g. cyanomethyl ester, methoxymethyl ester, dimethyliminomethyl [$(CH_3)_2N^+=CH-$] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc.], and the like. These reactive derivatives can optionally be selected from them according to the kind of the compound [III] to be used.

Suitable salts of the compound [III] and its reactive derivative can be referred to the ones as exemplified for the compound [I].

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

In this reaction, when the compound [III] is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N'carbonylbis-(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; thionyl chloride; oxalyl chloride; lower alkyl haloformate [e.g. ethyl chloroformate, isopropyl chloroformate, etc.]; triphenylphosphine; 2-ethyl-7-hydroxybenzisoxazolium salt; 2-ethyl-5-(m-sulfophenyl)isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorus oxychloride, etc.; or the like.

The reaction may also be carried out in the presence of an inorganic or organic base such as an alkali metal bicarbonate, tri(lower)alkylamine, pyridine, N-(lower)alkylmorpholine, N,N-di(lower)alkylbenzylamine, or the like.

The reaction temperature is not critical, and the reaction is usually carried out under cooling to warming.

Process 2

The object compound [Ib] or a salt thereof can be prepared by subjecting a compound [Ia] or a salt thereof to elimination reaction of the carboxy protective group.

This reaction is carried out in accordance with a conventional method such as hydrolysis, reduction or the like.

The hydrolysis is preferably carried out in the presence of base or an acid including Lewis acid. Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, trialkylamine [e.g. trimethylamine, triethylamine, etc.], picoline, 1,5-diazabicyclo[4.3.0]non-5-ene, 1,4-diazabicyclo[2.2.2]octane, 1,8-diazabicyclo[5.4.0]-undec-7-ene, or the like. Suitable acid may include an organic acid [e.g. formic acid, acetic acid, propionic acid, trichloroacetic acid, trifluoroacetic acid, etc.] and an inorganic acid [e.g. hydrochloric acid, hydrobromic acid, sulfuric acid, hydrogen chloride, hydrogen bromide, etc.]. The elimination using Lewis acid such as trihaloacetic acid [e.g. trichloroacetic acid, trifluoroacetic acid, etc.] or the like is preferably carried out in the presence of cation trapping agents [e.g. anisole, phenol, etc.].

The reaction is usually carried out in a solvent such as water, an alcohol [e.g. methanol, ethanol, etc.], methylene chloride, tetrahydrofuran, a mixture thereof or any other solvent which does not adversely influence the reaction. A liquid base or acid can be also used as the solvent. The reaction temperature is not critical and the reaction is usually carried out under cooling to warming.

The reduction method applicable for the elimination reaction may include chemical reduction and catalytic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalysts [e.g. platinum plate, spongy platinum, platinum black, colloidal platinum, platinum oxide, platinum wire, etc.], palladium catalysts [e.g. spongy palladium, palladium black, palladium oxide, palladium on carbon, colloidal palladium, palladium on barium sulfate, palladium on barium carbonate, etc.], nickel catalysts [e.g. reduced nickel, nickel oxide, Raney nickel, etc.], cobalt catalysts [e.g. reduced cobalt, Raney cobalt, etc.], iron catalysts [e.g. reduced iron, Raney iron, etc.], copper catalysts [e.g. reduced copper, Raney copper, Ullman copper, etc.] and the like.

The reduction is usually carried out in a conventional solvent which does not adversely influence the reaction such as water, methanol, ethanol, propanol, N,N-dimethylformamide, or a mixture thereof. Additionally, in case that the abovementioned acids to be used in chemical reduction are in liquid, they can also be used as a solvent. Further, a suitable solvent to be used in catalytic reduction may be the abovementioned solvent, and other conventional solvent such as diethyl ether, dioxane, tetrahydrofuran, etc., or a mixture thereof.

The reaction temperature of this reduction is not critical and the reaction is usually carried out under cooling to warming.

Process 3

The object compound [I] or a salt thereof can be prepared by reacting a compound [VII] or a salt thereof with a compound [V] or a salt thereof.

Suitable salts of the compounds [V] and [VII] can be referred to the ones as exemplified for the compound [I].

The present reaction may be carried out in a solvent such as water, phosphate buffer acetone, chloroform, acetonitrile, nitrobenzene, methylene chloride, ethylene chloride, formamide, N,N-dimethylformamide, methanol, ethanol, diethyl ether, tetrahydrofuran, dimethyl sulfoxide, or any other organic solvent which does not adversely affect the reaction, preferably in ones having strong polarities. Among the solvents, hydrophilic solvents may be used in a mixture with water. When the compound [V] is in liquid, it can also be used as a solvent. The reaction is preferably conducted in the presence of a base, for example, inorganic base such as alkali metal hydroxide, alkali metal carbonate, alkali metal bicarbonate, organic base such as trialkylamine, and the like. The reaction temperature is not critical, and the reaction is usually carried out at ambient temperature, under warming or under heating. The present reaction is preferably carried out in the presence of alkali metal halide [e.g. sodium iodide, potassium iodide, etc.], alkali metal thiocyanate [e.g. sodium thiocyanate, potassium thiocyanate, etc.] or the like.

The starting compound [II] is novel and can be prepared by the following processes A and B.

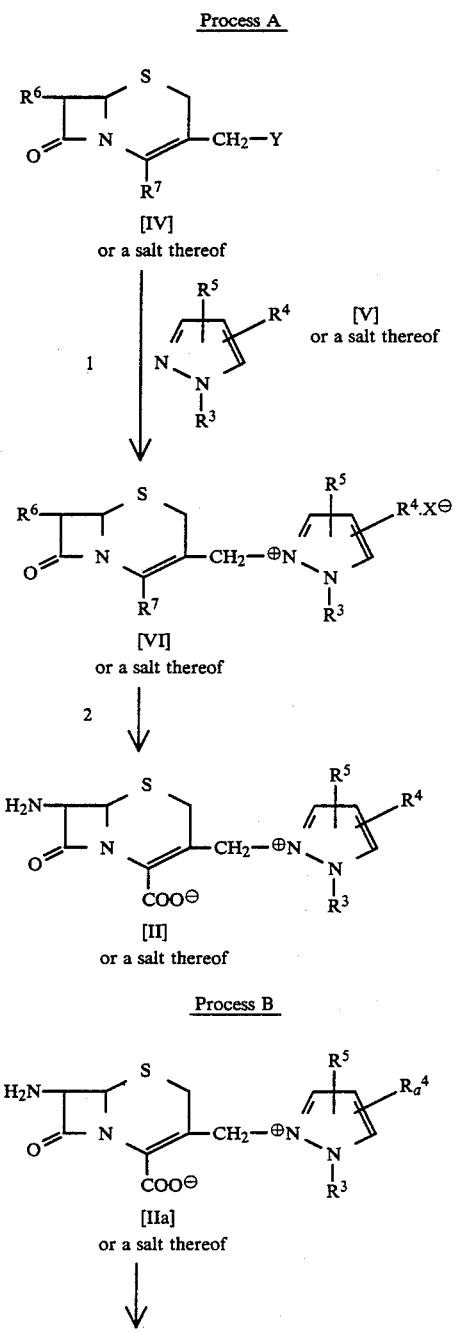

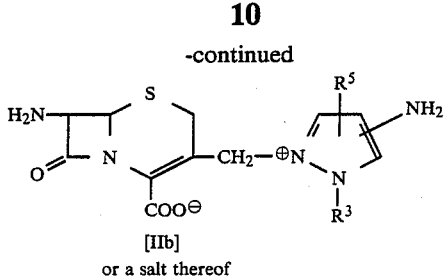

wherein
$R^3$, $R^4$, $R^5$ and Y are each as defined above,
$R^6$ is a protected amino group,
$R^7$ is a protected carboxy group,
$X^\ominus$ is an anion, and
$R_a^4$ is a protected amino group.

Suitable "protective group" in the "protected amino group" for $R^6$ can be referred to the ones as exemplified before and the preferred one may be substituted or unsubstituted ar(lower)alkylidene (e.g., benzylidene, hydroxybenzylidene, etc.), lower alkoxycarbonyl, (e.g., methoxycarbonyl, ethoxycarbonyl, tert-butoxycarbonyl, tert-pentyloxycarbonyl, hexyloxycarbonyl, etc.).

Suitable "protected carboxy group" for $R^7$ can be referred to the ones as exemplified before and the preferred one may be ar(lower)alkoxycarbonyl which may have suitable substituent(s) (e.g. benzhydryloxycarbonyl, etc.).

Suitable "anion" may be formate, acetate, trifluoroacetate, maleate, tartrate, methanesulfonate, benzenesulfonate, toluenesulfonate, chloride, bromide, iodide, sulfate, phosphate, or the like.

Processes A and B for the preparation of the starting compound [II] is explained in detail in the following.

Process A - ①

The compound [VI] or a salt thereof can be prepared by reacting the compound [IV] or a salt thereof with the compound [V] or a salt thereof. This reaction can be carried out in a similar manner to that of the aforementioned Process 3, and therefore the reagents to be used and the reaction conditions (e.g., solvent, reaction temperature, etc.) can be referred to those of the Process 3.

Anion $X^\ominus$ may be the one derived from a leaving group Y and may be the other one converted therefrom by a conventional method.

Process A - ②

The compound [II] or a salt thereof can be prepared by subjecting the compound [VI] or a salt thereof to elimination reaction of the amino protective group in $R^6$ and the carboxy protective group in $R^7$.

This reaction is carried out in accordance with a conventional method such as hydrolysis or the like.

The hydrolysis is preferably carried out in the presence of a base or an acid including Lewis acid. Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, trialkylamine [e.g. trimethylamine, triethylamine, etc.], picoline, 1,5-diazabicyclo-[4.3.0]non-5-ene, 1,4-diazabicyclo[2.2.2]octane, 1,8-diazabicyclo[5.4.0]undec-7-ene, or the like. Suitable acid may include an organic acid [e.g. formic acid, acetic acid, propionic acid, trichloroacetic acid, trifluoroacetic acid, etc.] and an inorganic acid [e.g. hydrochloric acid, hydrobromic acid, sulfuric acid, hydrogen chloride, hydrogen bromide, etc.]. The elimination using Lewis acid such as trihaloacetic acid [e.g. trichloroacetic acid, trifluoroacetic acid, etc.] or the like is preferably carried out in the presence of cation trapping agents [e.g. anisole, phenol, etc.].

The reaction is usually carried out in a solvent such as water, an alcohol [e.g. methanol, ethanol, etc.], methylene chloride, tetrahydrofuran, a mixture thereof or any other solvent which does not adversely influence the reaction. A liquid base or acid can be also used as the solvent. The reaction temperature is not critical and the reaction is usually carried out under cooling to warming.

The present invention includes within the scope of the invention the case that protected amino in $R^4$ is transformed into amino during this reaction.

Process B

The compound [IIb] or a salt thereof can be prepared by subjecting the compound [IIa] to elimination reaction of the amino protective group in $R_a^4$. This reaction can be carried out in a simila that of the aforementioned Process A -②, therefore the reagents to be used and the reaction conditions (e.g., solvent, reaction temperature, etc.) can be referred to those of the Process A -②. The present invention includes within the scope of the invention the case that protected hydroxy(lower)alkyl in $R^3$ is transformed into hydroxy(lower)alkyl during this reaction.

The object compounds [I] and pharmaceutically acceptable salts thereof are novel and exhibit high antimicrobial activity, inhibiting the growth of a wide variety of pathogenic microorganisms including Gram-positive and Gram-negative microorganisms and are useful as antimicrobial agents.

Now in order to show the utility of the object compounds [I], the test data on MIC (minimal inhibitory concentration) of representative compounds [I] of this invention are shown in the following.

Test method

In vitro antibacterial activity was determined by the two-fold agar-plate dilution method as described below.

One loopful of an overnight culture of each test strain in Trypticase-soy broth ($10^6$ viable cells per ml) was streaked on heart infusion agar (HI-agar) containing graded concentrations of representative test compound, and the minimal inhibitory concentration (MIC) was expressed in terms of μg/ml after incubation at 37° C. for 20 hours.

Test compounds (1) 7β-[2-(5-Amino-1,2,4-thiadiazol-3-yl)-2-carboxymethoxyiminoacetamido]-3-(3-amino-2-methyl-1-pyrazolio)methyl-3-cephem-4-carboxylate (syn isomer) (hereinafter referred to as Compound A).

(2) 7β-[2-(5-Amino-1,2,4-thiadiazol-3-yl)-2-carboxymethoxyiminoacetamido]-3-(3-formamido-2-methyl-1-pyrazolio)-methyl-3-cephem-4-carboxylate (syn isomer) (hereinafter referred to as Compound B).

(3) 7β-[2-(5-Amino-1,2,4-thiadiazol-3-yl)-2-(1-carboxy-1-methylethoxyimino)acetamido]-3-(3-amino-2-methyl-1-pyrazolio)methyl-3-cephem-4-carboxylate (syn isomer) (hereinafter referred to as Compound C).

Test results

| Test strain | MIC (μg/ml) Test compounds | | |
| --- | --- | --- | --- |
| | A | B | C |
| P. vulgaris 49 | 0.20 | 0.20 | 0.10 |

For therapeutic administration, the object compounds [I] and pharmaceutically acceptable salts thereof of the present invention are used in the form of conventional pharmaceutical preparation which contains said compound as an active ingredient, in admixture with pharmaceutically acceptable carriers such as an organic or inorganic solid or liquid excipient which is suitable for oral, parenteral and external administration. The pharmaceutical preparations may be in solid form such as tablet, granule, powder, capsule, or liquid form such as solution, suspension, syrup, emulsion, lemonade and the like.

If needed, there may be included in the above preparations auxiliary substances, stabilizing agents, wetting agents and other commonly used additives such as lactose, citric acid, tartaric acid, stearic acid, magnesium stearate, terra alba, sucrose, corn starch, talc, gelatin, agar, pectin, peanut oil, olive oil, cacao butter, ethylene glycol, and the like.

While the dosage of the compound [I] may vary from and also depend upon the age, conditions of the patient, a kind of diseases, a kind of the compound [I] to be applied, etc. In general, amounts between 1 mg and about 4,000 mg or even more per day may be administered to a patient. An average single dose of about 50 mg, 100 mg, 250 mg, 500 mg, 1000 mg, 2000 mg of the object compounds [I] of the present invention may be used in treating diseases infected by pathogenic microorganisms.

The following Preparations and Examples are given for the purpose of illustrating the present invention in more detail.

PREPARATION 1

A mixture of acetic anhydride (38.86 ml) and formic acid (15.54 ml) was stirred at 45° C. for 45 minutes. To this mixture was added 5-amino-1-methylpyrazole (10 g) under ice-cooling, and the reaction mixture was stirred at the same temperature for 10 minutes. The resultant mixture was poured into a mixture of water and ethyl acetate, and the resultant solution was adjusted to pH 8 with potassium carbonate. The organic layer was separated, and the aqueous layer was extracted with ethyl acetate six times. The organic layers were combined, dried over magnesium sulfate, and evaporated in vacuo to give 5-formamido-1-methylpyrazole (12.88 g).

mp:71–73° C.
IR (Nujol) : 3300, 3200, 1705, 1590 cm$^{-1}$
NMR (CDCl$_3$, δ) : 3.69 and 3.74 (3H, each s),
6.04 and 6.23 (1H, each d, J=3Hz),
7.34 (1H, s), 8.21 (1H, s)

PREPARATION 2

The following compounds were obtained according to a similar manner to that of Preparation 1.
(1) 4-Formamido-1-methylpyrazole
mp: 44–45° C.
IR (Nujol) : 3250, 1665, 1585 cm$^{-1}$ NMR (CDCl$_3$, δ):3.83 (3H, s), 7.33 (1H, s), 7.83 (1H, s), 8.17 (1H, s)

(2) 5-Formamido-1,4-dimethylpyrazole

IR (Nujol) : 3200, 1665, 1585 cm$^{-1}$

NMR (CDCl$_3$, δ) : 1.90 and 1.98 (3H, each s), 3.64 and 3.72 (3H, each s), 7.29 and 7.31 (1H, each s), 8.10 (1H, broad s), 8.33 and 9.03 (1H, each s).

PREPARATION 3

To a mixture of benzhydryl 7δ-tert-butoxycarbonylamino-3-chloromethyl-3-cephem-4-carboxylate (15 g) and sodium iodide (4.37 g) in acetone (15 ml) was added 5-fomamido-1-methylpyrazole (15 g) at ambient temperature. After being stirred for 40 hours at the same temperature, the mixture was poured into a mixture of water and ethyl acetate. The organic layer was separated and washed with water, aqueous sodium chloride solution, and dried over magnesium sulfate.

The solution was evaporated in vacuo to give benzhydryl 7β-tert-butoxycarbonylamino-3-(3-formamido-2-methyl-1-pyrazolio)methyl-3-cephem.4-carboxylate iodide (20.95 g).

IR (Nujol) : 1780, 1710, 1580 cm$^{-1}$

NMR (DMSO-d$_6$, δ) : 1.40 (9H, s), 3.41 (2H, broad s), 3.65 (3H, s), 5.12 (1H, d, J=5Hz), 5.36 (2H, broad s), 5.57 (1H, dd, J=8Hz and 5Hz), 6.88 (1H, s), 6.89 (1H, m), 7.10–7.48 (10H, m), 7.83 (1H, d, J=8Hz), 8.24 (1H, d, J=3Hz), 8.45 (1H, s)

PREPARATION 4

The following compounds were obtained according to a similar manner to that of Preparation 3.

(1) Benzhydryl 7β-tert-butoxycarbonylamino-3-(4-formamido-2-methyl-1-pyrazolio)methyl-3-cephem-4-carboxylate iodide IR (Nujol) : 1785, 1720, 1605 cm$^{-1}$ NMR (DMSO-d$_6$, δ) : 1.39 (9H, s), 3.42 (2H, broad s), 3.77 (3H, s), 5.11 (1H, d, J=5Hz), 5.41 (2H, broad s), 5.60 (1H, dd, J=8Hz and 5Hz), 6.89 (1H, s), 7.18–7.52 (10H, m), 7.96 (1H, d, J=8Hz), 8.25 (1H, s), 8.51 (1H, s), 8.57 (1H, s).

(2) Benzhydryl 7β-tert-butoxycarbonylamino-3-(3-formamido-2,4-dimethyl-1-pyrazolio)methyl-3-cephem-4-carboxylate iodide.

IR (Nujol) : 3300, 1780, 1705 cm$^{-1}$

NMR (DMSO-d$_6$, δ) : 1.42 (9H, s), 1.98 (3H, s), 3.45 (2H, broad s), 3.63 (3H, s), 5.19 (1H, d, J=5Hz), 5.40 (2H, broad s), 5.61 (1H, dd, J=5Hz and 8Hz), 6.95 (1H, s), 7.21–7.58 (10H, m), 8.00 (1H, d, J=8Hz), 8.21 (1H, s), 8.43 (1H, s)

PREPARATION 5

To a solution of benzhydryl 7β-tert-butoxycarbonylamino-3-(3-formamido-2-methyl-1 -pyrazolio)-methyl-3-cephem-4-carboxylate iodide (20.9 g) and anisole (20 ml) in methylene chloride (40 ml) was added dropwise trifluoroacetic acid (40 ml) under ice-cooling. After being stirred for 1.5 hours at ambient temperature, the mixture was poured into a mixture of diisopropyl ether (300 ml) and ethyl acetate (300 ml). The resultant precipitate was collected by filtration to give di(trifluoroacetic acid) salt of 7β-amino-3-(3-formamido-2-methyl-1-pyrazolio)-methyl-3-cephem-4-carboxylate (16.20 g).

IR (Nujol) : 3350, 1770, 1660 cm$^{-1}$

NMR (DMSO-d$_6$, δ) : 3.45 (2H, s), 3.87 (3H, s), 5.18 (2H, s), 5.47 (2H, s), 6.95 (1H, d, J=3Hz), 8.33 (1H, d, J=3Hz), 8.47 (1H, s).

PREPARATION 6

The following compounds were obtained according to a similar manner to that of Preparation 5.

(1) Di(trifluoroacetic acid)salt of 7β-amino-3-(4-formamido-2-methyl-1-pyrazolio)methyl-3-cephem-4-carboxylate.

IR (Nujol) : 3400, 1780, 1660, 1605 cm$^{-1}$

NMR (DMSO-d$_6$, δ) : 3.51 (2H, broad s), 4.06 (3H, s), 5.23 (2H, s), 5.55 (2H, broad s), 8.30 (1H, s), 8.61 (1H, s), 8.67 (1H, s).

(2) Di(trifluoroacetic acid)salt of 7β-amino-3-(3-formamido-2,4-dimethyl-1-pyrazolio)methyl-3-cephem-4-carboxylate.

NMR (DMSO- d$_6$, δ) : 2.01 (3H, s), 3.48 (2H, broad s), 3.83 (3H, s), 5.24 (2H, s), 5.50 (2H, broad s), 8.26 (1H, s), 8.41 (1H, s).

PREPARATION 7

Concentrated hydrochloric acid (0.353 ml) was added to a mixture of di(trifluoroacetic acid)salt of 7β-amino-3-(3-formamido-2-methyl-1-pyrazolio)methyl-3-cephem-4-carboxylate (0.565 g) in tetrahydrofuran (3 ml) and methanol (3 ml) at ambient temperature. After being stirred at the same temperature for 12 hours, the mixture was added dropwise to ethyl acetate (100 ml). The resultant precipitate was collected by filtration to give 7β-amino-3-(3-amino-2-methyl-1-pyrazolio)methyl-3-cephem-4-carboxylate trihydrochloride (292 mg).

NMR (DMSO-d$_6$, δ) : 3.31 and 3.56 (2H, ABq, J=18 Hz), 3.67 (3H, s), 5.20 (2H, broad s), 5.29 (2H, broad s), 5.87 (1H, d, J=3Hz), 8.12 (1H, d, J=3Hz)

PREPARATION 8

7β-Amino-3-(3-amino-2,4-dimethyl-1-pyrazolio)-methyl-3-cephem-4-carboxylate trihydrochloride was obtained according to a similar manner to that of Preparation 7.

IR (Nujol) : 3350, 1780, 1640 cm$^{-1}$

NMR (DMSO-d$_6$, δ) : 1.97 (3H, s), 3.49 (2H, s), 3.74 (3H, s), 5.27 (4H, s), 8.00 (1H, s).

EXAMPLE 1

To a solution of di(trifluoroacetic acid)salt of 7β-amino-3-(4-formamido-2-methyl-1-pyrazolio)methyl-3-cephem-4-carboxylate (4.0 g) and N-(trimethylsilyl)acetamide (9.29 g) in tetrahydrofuran (60 ml) was added methanesulfonyl (Z)-2-(5-amino-1,2,4-thiadiazol-3-yl)-2-carboxymethoxyiminoacetate (2.07 g) under ice-cooling. The mixture was stirred for 1 hour at ambient temperature and then the resulting mixture was added dropwise to diisopropyl ether. Thus produced precipitate was collected by filtration, dissolved in water and then subjected to column chromatography on macroporous non-ionic adsorption resin, Diaion HP-20 (Trademark: manufactured by Mitsubishi Chemical Industries). The desired product was eluted with 10% aqueous isopropyl alcohol solution, and then lyophilized to give 7β-[2-(5-amino-1,2,4-thiadiazol-3-yl)-2-carboxymethoxyiminoacetamido]-3- (4-formamido-2-methyl-1-pyrazolio)methyl-3-cephem-4-carb oxylate (syn isomer 0.714 g).

IR (Nujol) : 3300, 1765, 1665, 1605 cm$^{-1}$

NMR (D$_2$O, δ) : 3.18 and 3.51 (2H, ABq, J=18Hz), 4.09 (3H, s), 4.63 (2H, s), 5.22 and 5.46 (2H, ABq, J=15Hz), 5.23 (1H, d, J=5Hz), 5.86 (1H, d, J=5Hz), 8.25 (1H, s), 8.36 (1H, s), 8.43 (1H, s)

EXAMPLE 2

(1) 7β-[2-(5-Amino-1,2,4-thiadiazol-3-yl)-2-carboxymethoxyiminoacetamido]-3-(3-formamido-2-methyl-1-pyrazolio)methyl-3-cephem-4-carboxylate (syn isomer) was obtained according to a similar manner to that of Example 1.

IR (Nujol) : 3300, 1760, 1660, 1580 cm$^{-1}$

NMR (D$_2$O, δ) : 3.13 and 3.44 (2H, ABq, J=18Hz), 3.91 (3H, s), 4.67 (2H, s), 5.21 (1H, d, J=5Hz), 5.22 and 5.43 (2H, ABq, J=15Hz), 5.85 (1H, d, J=5Hz), 6.82 and 6.92 (1H, each d, J=3Hz), 8.15 (1H, d, J=3Hz), 8.40 (1H, s).

(2) 7β-[2-(5-Amino-1,2,4-thiadiazol-3-yl)-2-carboxymethoxyiminoacetamido]-3-(3-formamido-2,4-dimethyl-1-pyrazolio)methyl-3-cephem-4-carboxylate (syn isomer) was obtained according to a similar manner to that of Example 1.

IR (Nujol) : 3300, 1765, 1660, 1600 cm$^{-1}$

NMR (D$_2$O, δ) : 2.03 (3H, s), 3.17 and 3.48 (2H, ABq, J=18Hz), 3.83 (3H, s), 4.70 (2H, s), 5.18 and 5.43 (2H, ABq, J=15Hz), 5.24 (1H, d, J=5Hz), 5.87 (1H, d, J=5Hz), 8.05 (1H, s), 8.36 (1H, s)

EXAMPLE 3

To a solution of 7β-amino-3-(3-amino-2-methyl-1-pyrazolio)methyl-3-cephem-4-carboxylate trihydrochloride (6.96 g) and N-(trimethylsilyl)acetamide (21.8 g) in tetrahydrofuran (150 ml) was added methanesulfonyl (Z)-2-(5-amino-1,2,4-thiadiazol-3-yl)-2-carboxymethoxyiminoacetate (4.86 g) at ambient temperature. After being stirred for 30 minutes at the same temperature, the mixture was poured into diethyl ether (2 l), and the resultant precipitate was collected by filtration. The precipitate was dissolved in water, and the solution was adjusted to pH 2.0 with aqueous sodium bicarbonate solution. The solution was subjected to column chromatography on macroporous non-ionic adsorption resin, Diaion HP-20. The desired product was eluted with 5% isopropyl alcohol solution and lyophilized to give 7β[2-(5-amino-1,2,4-thiadiazol-3-yl)-2-carboxymethoxyiminoacetamido]-3-(3-amino-2-methyl-1-pyrazolio)-methyl-3-cephem-4-carboxylate (syn isomer)(5.20 g).

IR (Nujol) : 3300, 1760, 1660, 1590 cm$^{-1}$

NMR (D$_2$O, δ) : 3.06 and 3.33 (2H, ABq, J=18Hz), 3.63 (3H, s), 4.60 (2H, s), 4.93 and 5.21 (2H, ABq, J=15Hz), 5.16 (1H, d, J=5Hz), 5.83 (1H, d, J=5Hz), 5.88 (1H, d, J=3Hz), 7.78 (1H, d, J=3Hz).

EXAMPLE 4

To a solution of 7β-amino-3-(3-amino-2,4-dimethyl-1-pyrazolio)methyl-3-cephem-4-carboxylate trihydrochloride (1.0 g) and N-(trimethylsilyl)-acetamide (3.03 g) in tetrahydrofuran (20 ml) was added methanesulfonyl (Z)-2-(5-amino-1,2,4-thiadiazol-3-yl)-2-carboxymethoxyiminoacetate (0.68 g) at ambient temperature. After being stirred for 1 hour at the same temperature, the mixture was poured into diethyl ether (300 ml) and the resultant precipitate was collected by filtration. The precipitate was dissolved in water and the solution was adjusted to pH 2.0 with aqueous sodium bicarbonate solution.

The solution was subjected to a column chromatography on macroporous non-ionic adsorption resin, Diaion HP-20. The desired product was eluted with 5% isopropyl alcohol aqueous solution and lyophilized to give 7β-[2-(5-amino-1,2,4-thiadiazol-3-yl)-2-carboxymethoxyiminoacetamido]-3-(3-amino-2,4-dimethyl-1-pyrazolio)methyl-3-cephem-4-carboxylate (syn isomer)(0.165 g).

IR (Nujol) : 3350, 1770, 1660, 1600 cm$^{-1}$

NMR (D$_2$O, δ) 1.93 (3H, s), 3.06 and 3.30 (2H, ABq, J=18Hz), 3.64 (3H, s), 4.67 (2H, s), 4.88 and 5.19 (2H, ABq, J=15Hz), 5.18 (1H, d, J=5Hz), 5.84 (1H, d, J=5Hz), 7.66 (1H, s).

PREPARATION 9

To a solution of phosphorus pentachloride (11.11 g) in methylene chloride (167.8 ml) was added (Z)-2-(5-amino-1,2,4-thiadiazol-3-yl)-2-(1-tert-butoxycarbonyl-1-methylethoxyimino)acetic acid (16.78 g) at −20° C. The resultant mixture was stirred at −20 to −10° C. for 1.5 hours, and to the mixture was added dropwise diisopropyl ether (671.2 ml) at −20 to −10° C. The mixture was stirred under ice-cooling for 1 hour and the resultant precipitate was collected by filtration to give (Z)-2-(5-amino-1,2,4-thiadiazol-3-yl)-2-(1-tert-butoxycarbonyl-1-methylethoxyimino)acetyl chloride hydrochloride (14.8 g).

IR (Nujol) : 3430, 3270, 3130, 1815, 1750, 1725, 1640 cm$^{-1}$

EXAMPLE 5

To a solution of 7β-amino-3-(3-amino-2-methyl-1-pyrazolio)methyl-3-cephem-4-carboxylate trihydrochloride (2 g) and N-(trimethylsilyl)acetamide (6.28 g) in tetrahydrofuran (40 ml) was added (Z)-2-(5-amino-1,2,4-thiadiazol-3-yl)-2-(1-tert-butoxycarbonyl-1-methyl-yl-ethoxyimino)acetyl chloride hydrochloride (1.84 g) under ice-cooling. After being stirred for 1 hour, the reaction was added dropwise to ethyl ether (300 ml), and the resulting precipitate was collected by filtration to give 7β-[2-(5-amino-1,2,4-thiadiazol-3-yl)-2-(1-tert-butoxycarbonyl-1-methylethoxyimino)-acetamido]-3-(3-amino-2-methyl-1pyrazolio)methyl-3-cephem-4 -carboxylate trihydrochloride (syn isomer) (3.4 g).

IR (Nujol) : 3300, 1780, 1720, 1650 cm$^{-1}$

NMR (D$_2$O, δ) : 1.45 (9H, s), 1.57 (6H, s), 3.09 and 3.37 (2H, ABq, J=18Hz), 3.67 (3H, s), 4.98 and 5.27 (2H, ABq, J=15Hz), 5.21 (1H, d, J=5Hz), 5.86 (1H, d, J=5Hz), 5.92 (1H, d, J=3Hz), 7.85 (1H, d, J=3Hz)

EXAMPLE 6

The following compounds were obtained according to similar manners to those of Examples 1,3,4 and 5.

(1) 7β-[2-(5-Amino-1,2,4-thiadiazol-3-yl)2-(1-tert-butoxycarbonyl-1-methylethoxyimino)acetamido]-3-(3-amino-2,4-dimethyl-1-pyrazolio)methyl-3- cephem-4-c arboxylate trihydrochloride (syn isomer)

IR (Nujol) : 3300, 1780, 1650 cm$^{-1}$

NMR (D$_2$O, δ) : 1.42 (9H, s), 1.47 (6H, s), 1.93 (3H, s), 3.32 (2H, broad s), 3.67 (3H, s), 5.18 (2H, broad s), 5.22 (1H, d, J=5Hz), 5.90 (1H, dd, J=8Hz, 5Hz), 7.90 (1H, s), 9.45 (1H, d, J=8Hz)

(2) 7β-[2-(5-Amino-1,2,4-thiadiazol-3-2-(1-carboxy-1-methylethoxyimino)acetamido]-3-(3-amino-2,4-dimethyl-1-pyrazolio)methyl-3-cephem-4-carboxylate (syn isomer)

IR (Nujol) : 3320, 3180, 1760, 1650, 1595 cm$^{-1}$ (3) 7β-[2-(5-Amino-1,2,4-thiadiazol-3-yl)-2-(1-carboxy-1- methyethoxyimino)acetimido]-3-(2-methyl-formamido-1-pyrazolio)methyl-3-cephem-4-carboxylate (syn isomer)

IR (Nujol) : 3320, 3180, 1760, 1650, 1595 cm$^{-1}$

NMR (DMSO-d$_6$, δ) : 1.46 (6H, s), 3.05–3.37 (2H, m), 3.91 (3H, s), 4.90–5.57 (2H, m), 5.06 (1H, d, J=5Hz), 5.71 (1H, dd, J=5, 8Hz), 6.91 (1H, d, J=3Hz), 8.02-8.27 (2H, br s), 8.34 (1H, d, J=3Hz), 8.56 (1H, s), 9.46 (1H, d, J=8Hz)

(4) 7β[2-(5-Amino-1,2,4-thiadiazol-3-yl)-2-(1-carboxy-1-methylethoxyimino)acetamido]-3-]3-amino-2-(2-hydroxyethyl)-1-pyrazolio]methyl-3-cephem-4carboxylate (syn isomer)

IR (Nujol) : 3300, 1765, 1640 cm$^{-1}$

NMR (D$_2$O, δ) : 1.58 (6H, s), 3.10 and 3.43 (2H, ABq, J=18Hz), 3.78-3.97 (2H, m), 4.26-4.46 (2H, m), 5.15 (2H, br s), 5.26 (1H, d, J=5Hz), 5.87 (1H, d, J=5Hz), 5.97 (1H, d, J=3Hz), 7.89 (1H, d, J=3Hz)

(5) 7β-[2-(5-Amino-1,2,4-thiadiazol-3-yl)-2-(1-carboxy-1-2-methyl-1-pyrazolio)methyl-3-cephem-4-carboxylate (syn isomer)

IR (Nujol) : 3300, 1775, 1670 cm$^{-1}$

NMR (D$_2$O, δ) : 1.56 (6H, s), 2.31 (3H, s), 3.20 and 3.50 (2H, ABq, J=18Hz), 3.93 (3H, s), 5.23 and 5.47 (2H, ABq, J=15Hz), 5.26 (1H, d, J=5Hz), 5.88 (1H, d, J=5Hz), 6.88 (1H, d, J=3Hz), 8.19 (1H, d, J=3Hz)

(6) 7β-[2-(5- Amino-1,2,4-thiadiazol-3-yl)-2-(1-carboxy-1-methylethoxyimino)acetamido]-3-(2-methyl-3-ureido-1-pyrazolio)methyl-3-cephem-4-carboxylate (syn isomer)

IR (Nujol) : 3300 (broad s), 1770, 1680, 1570 cm$^{-1}$

EXAMPLE 7

Trifluoroacetic acid (7 ml) was added dropwise to a suspension of 7β-[2-(5-amino-1,2,4-thiadiazol-3-yl)-2-(1-tert-butoxycarbonyl-1-methylethoxyimino)acetamido]-3-(3-amino-2-methyl-1-pyrazolio)methyl-3-cephem-4-carb oxylate trihydrochloride (3.3 g) and anisole (3.5 ml) in methylene chloride (10 ml) at ambient temperature. After being stirred at the same temperature for 4 hours, the mixture was poured into diisopropyl ether (300 ml), and the resulting precipitate was collected by filtration. The precipitate was dissolved in water (100 ml), and the solution was adjusted to pH 2 with 5% aqueous solution of sodium bicarbonate. The aqueous solution was subjected to column chromatography on macroporous non-ionic adsorption resin "Diaion HP-20". The desired product was eluted with 5% aqueous isopropyl alcohol solution and lyophilized to give 7β-[2-(5-amino-1,2,4-thiadiazol-3-yl)-2-(l-carboxy-1-methylethoxy-imino)acetamido]-3-(3-amino-2-methyl-1-pyrazolio)methyl-3-cephem-4-ca rboxylate (syn isomer) (515 mg).

IR (Nujol) : 3325, 1770, 1650, 1630, 1590 cm$^{-1}$

NMR (D$_2$O, δ) : 1.52 (6H, s), 3.19 and 3.37 (2H, ABq, J=18Hz), 3.66 (3H, s), 4.97 and 5.25(2H, ABq, J=15Hz), 5.20 (1H, d, J=5Hz), 5.84 (1H, d, J=5Hz), 5.91 (1H, d, J=3Hz), 7.82 (1H, d, J=3Hz)

EXAMPLE 8

The following compounds were obtained according to a similar manner to that of Example 7.

(1) 7β-[2-(5-Amino-1,2,4-thiadiazol-3-yl)-2-(1-carboxy-1-methylethoxyimino)acetamido]-3-(3-amino-2,4-dimethyl-1-pyrazolio)methyl-3-cephem-4-carboxylate (syn isomer)

IR (Nujol) : 3320, 3180, 1760, 1650, 1595 cm$^{-1}$

NMR (D$_2$O, δ) : 1.60 (6H, s), 1.96 (3H, s), 3.10 and 3.37 (2H, ABq, J=18Hz), 3.68 (3H, s), 4.92 and 5.23 (2H, ABq, J=15Hz), 5.22 (1H, d, J=5Hz), 5.86 (1H, d, J=5Hz), 7.68 (1H, s)

(2) 7β-[2-(5-Amino-1,2,4-thiadiazol-3-yl)-2-carboxymethoxyiminoacetamido]-3-(4-formamido-2-methyl-1-pyrazolio)methyl-3-cephem-4-carboxylate (syn isomer)

IR (Nujol) : 3300, 1765, 1665, 1605 cm$^{-1}$ (3) 7β-[2-(5-Amino-1,2,4-thiadiazol-3-yl)-2-carboxymethoxyiminoacetamido]-3-(3-formamido-2-methyl-1-pyrazolio)methyl-3-cephem-4-carboxylate (syn isomer)

IR (Nujol) : 3300, 1760, 1660, 1580 cm$^{-1}$ (4) 7β-[2-(5-Amino-1,2,4-thiadiazol-3-yl)-2-carboxymethoxyiminoacetamido]-3-(3-formamido-2,4-dimethyl-1-pyrazolio)methyl-3-cephem-4-carboxylate (syn isomer)

IR (Nujol) : 3300, 1765, 1660, 1600 cm$^{-1}$ (5) 7β-[2-(5-Amino-1,2,4-thiadiazol-3-yl)-2-carboxymethoxyiminoacetamido]-3-(3-amino-2-methyl-1-pyrazolio)methyl-3-cephem-4-carboxylate (syn isomer)

IR (Nujol) : 3300, 1760, 1660, 1590 cm$^{-1}$ (6) 7β-[2-(5-Amino-1,2,4-thiadiazol-3-yl)-2-carboxymethoxyiminoacetamido]-3-(3-amino-2,4-dimethyl-1-pyrazolio)methyl-3-cephem-4-carboxylate (syn isomer)

IR (Nujol) : 3350, 1770, 1660, 1600 cm$^{-1}$ (7) 7β-[2-(5-Amino-1,2,4-thiadiazol-3-yl)-2-(l-carboxy-1-methylethoxyimino)acetamido]-3-(2-methyl-3-formamido-1-pyrazolio)methyl-3-cephem-4-carboxylate (syn isomer)

IR (Nujol) : 3200-3300, 1760, 1580 cm$^{-1}$ (8) 7β-[2-(5-Amino-1,2,4-thiadiazol-3-yl)-2-(l-carboxy-1-methylethoxyimino)acetamido]-3-[3-amino-2-(2-hydroxyethyl)-1-pyrazolio]methyl-3-cephem-4-carb boxylate (syn isomer) IR : (Nujol) : 3300, 1765, 1640 cm$^{-1}$ (9) 7β-[2-(5-Amino-1,2,4-thiadiazol-3-yl)-2-(l-carboxy-1-methylethoxyimino)acetamido]-3-(3-acetamido-2-methyl-1-pyrazolio)methyl-3-cephem-4-carboxylate (syn isomer)

IR (Nujol) : 3300, 1775, 1670 cm$^{-1}$

(10) 7β-[2-(5-Amino-1,2,4-thiadiazol-3-yl)-2-(1-carboxy-1-methylethoxyimino)acetamido]-3-(2-methyl-3-ureido-1-pyrazolio)methyl-3-cephem-4-carboxylate (syn isomer)

IR (Nujol) : 3300 (broad s), 1770, 1680, 1570 cm$^{-1}$

PREPARATION 10

To a solution of malononitrile (300 g) and acetic acid (54.6 g) in acetonitrile (2.1 l) was added sodium nitrite (313 g) at 60-65° C. After being stirred at the same temperature for an hour, ethyl 2-bromo-2-methylpropanoate (797 g) was added to the mixture at 65° C. After being refluxed for five hours, the mixture was cooled to the ambient temperature and allowed to stand overnight. The resulting mixture was poured into a mixture of water (4.2 ) and diisopropyl ether (4.2 l). The separated organic layer was washed with water and brine, dried over magnesium sulfate and evaporated under reduced pressure to give 2-(1-ethoxycarbonyl-1-methylethoxyimino)propanedinitrile (860 g).

IR (Neat) : 3000, 2250, 1750 cm$^{-1}$

NMR (CDCl$_3$, δ) : 1.30 (t, J=7Hz, 3H), 1.69 (s, 6H), 4.25 (q, J=7Hz, 2H)

PREPARATION 11

To a solution of ammonium acetate (1258 g) in methanol (8.54 l) were added 2-(1-ethoxycarbonyl-1-methylethoxyimino)propanedinitrile (854 g) and 28% ammonia water (568 ml). After the mixture was stirred at 20° C. for 15 hours, methanol was evaporated under reduced pressure. The residue was dissolved in a mixture of water (8 l) and tetrahydrofuran (8 l). After the aqueous layer was saturated with sodium chloride, the organic layer was separated and dried over magnesium sulfate.

Acetic acid (368 g) was added to the solution, then the mixture was evaporated under reduced pressure, and the residue was triturated with diisopropyl ether (8 l) to give 2-cyano-2-(1-ethoxycarbonyl-1-methylethoxyimino)acetamidine acetate (689.1 g).

IR (Nujol) : 1750, 1670 cm$^{-1}$

NMR (CDCl$_3$,δ) : 1.26 (t, J=7Hz, 3H), 1.67 (s, 6H), 2.00 (s, 3H), 4.23 (q, J=7Hz, 2H), 8.73 (broad s, 2H)

PREPARATION 12

To a solution of 2-cyano-2-(1-ethoxycarbonyl-1-methylethoxyimino)acetamidine acetate (685 g) in methanol (6.85 l) was added triethylamine (557 g) at −13 ~ −15° C. over a 20-minute period and then bromine (344 g) was added thereto at the same temperature over the same period. The solution was stirred at −13 ~ −15° C. for 15 minutes, then N,N-dimethylformamide (685 ml) was added to the solution at the same temperature, and a solution of potassium thiocyanate (209 g) in methanol (2.09 l) was added thereto at −13 ~ −15° C. over a 30-minute period. After being stirred at −5 ~0° C. for an hour, the solution was poured into a cold water (5 ~ 10° C.) and stirred for an hour under ice-cooling. The resulting precipitates were collected by filtration, washed with cold water and dried to give 2-(5-amino-1,2,4-thiadiazol-3-yl)-2-(1-ethoxycarbonyl-1-methylethoxyimino)acetonitrile (390 g).

IR (Nujol) : 3470, 3280, 3140, 1730, 1625, 1540 cm$^{-1}$

NMR (CDCl$_3$, δ) : 1.25 (t, J=7Hz, 3H), 1.67 (s, 6H), 4.23 (q, J=7Hz, 2H), 7.86 (broad s 2H).

PREPARATION 13

A mixture of 2-(5-amino-1,2,4-thiadiazol-3-yl)-2-(1-ethoxycarbonyl-1-methylethoxyimino)acetonitrile (8.4 g) in 2N sodium hydroxide was stirred at 60–65° C. for 6 hours, adjusted to pH 4.2 with 6N hydrochloric acid under ice-cooling and washed with ethyl acetate (100 ml). Tetrahydrofuran (120 ml) was added to the aqueous solution, and the solution was adjusted to pH 1.0 with 6N hydrochloric acid under ice-cooling and saturated with sodium chloride. The separated organic layer was evaporated under reduced pressure. The residue was dissolved in a saturated aqueous solution (90 ml) of sodium bicarbonate and activated carbon (200 mg) was added thereto. After insoluble material and activated carbon were removed by filtration, the solution was adjusted to pH 1.0 with 6N hydrochloric acid under ice-cooling. The resulting precipitates were collected by filtration, washed with cold water and dried to give a crude product (6.96 g).

The crude product was recrystallized from propyl alcohol (111 ml) to give (Z)-2-(5-amino-1,2,4-thiadiazol-3-yl)-2-(1-carboxy-1-methylethoxyimino)acetic acid (4.70 g).

IR ( Nujol) : 3430, 3280, 3130, 1740, 1680, 1635, 1540 cm$^{-1}$

NMR (DMSO-d$_6$, δ) : 1.46 (s, 6H), 8.23 (broad s, 2H)

PREPARATION 14

A solution of (Z)-2-(5-amino-1,2,4-thiadiazol-3-yl)-2-(1-tert-butoxycarbonyl-1-methylethoxyimino)acetic acid (17.8 g) and anisole (18 ml) in trifluoroacetic acid (36 ml) was stirred for 4.0 hours at room temperature. The reaction mixture was concentrated under reduced pressure and an aqueous solution of sodium bicarbonate was added thereto to adjust to pH 6.0. The aqueous solution was washed with ethyl acetate, adjusted to pH 3.8 with 6N hydrochloric acid and washed with ethyl acetate. The aqueous layer was separated and 6N hydrochloric acid was added thereto to adjust to pH 1.0. After the mixture was stirred for 10 minutes, the resultant precipitate was collected by filtration to give (Z)-2-(5-amino-1,2,4-thiadiazol-3-yl)-2-(1-carboxy-1-methylethoxyimino)acetic acid (13.0 g).

PREPARATION 15

To a solution of (Z)-2-(5-amino-1,2,4-thiadiazol-3-yl)-2-(1-carboxy-1-methylethoxyimino)acetic acid (2.74 g) in N,N-dimethylacetamide (45 ml) were added methanesulfonyl chloride (1.15 g) and potassium bicarbonate (1.20 g) under cooling in an ice bath. The mixture was stirred for 2.5 hours at 5° C. and poured into a cold mixture of water (200 ml), ethyl acetate (200 ml) and 1N hydrochloric acid (6 ml). The mixture was stirred for 5 minutes under cooling in an ice bath. The organic layer was separated, washed with cold water (200ml×2) and with a cold saturated aqueous solution of sodium chloride, dried over magnesium sulfate and evaporated. Toluene was added to the residue. To the mixture was added methylene chloride and the mixture was cooled for 10 minutes in an ice bath. The crystals were collected by filtration, washed with methylene chloride and air-dried to give methanesulfonyl (Z)-2-(5-amino-1,2,4-thiadiazol-3-yl)-2-(1-carboxy-1-methylethoxyimino)acetate (1.1 g).

EXAMPLE 9

A mixture of 7β-amino-3-(3-amino-2-methyl-1-pyrazolio)methyl-3-cephem-4-carboxylate trihydrochloride (0.42 g), N-(trimethylsilyl)acetamide (2.5 g) and tetrahydrofuran was stirred for 1.0 hour at room temperature.

Methanesulfonyl (Z)-2-(5-amino-1,2,4-thiadiazol-3-yl)-2-(1-carboxy-1-methylethoxyimino)acetate (350 mg) was added thereto at room temperature and stirred for 2.0 hours at the same temperature. The mixture was poured into diisopropyl ether (50 ml), and the precipitates were collected by filtration, dissolved in water (50 ml), adjusted to pH 2.0 with an aqueous solution of sodium bicarbonate and washed with ethyl acetate, and ethyl acetate in the aqueous layer was evaporated. The aqueous layer was subjected to column chromatography on macroporous non-ionic adsorption resin "Diaion HP-20" and the elution was carried out with 30% aqueous methyl alcohol solution. Methyl alcohol in the fractions containing the object compound was evaporated and the residue was lyophilized to give 7β-[2-(5-amino-1,2,4-thiadiazol-3-yl)-2-(1-carboxy-1-methylethoxyimino)-acetamido]-3-(3-amino-2-methyl-1-pyrazolio)methyl-3-cephem-4-carboxylate (syn isomer)(330 mg).

IR (Nujol) : 3325, 1770, 1650, 1630, 1590 cm$^{-1}$

NMR (D$_2$O, δ) : 1.52 (6H, s), 3.19 and 3.37 (2H, ABq, J=18Hz), 3.66 (3H, s), 4.97 and 5.25 (2H, ABq, J=15Hz), 5.20 (1H, d, J=5Hz), 5.84 (1H, d, J=5Hz), 5.91 (1H, d, J=3Hz), 7.82 (1H, d, J=3Hz).

PREPARATION 16

7β-Amino-3-(3-amino-2-methyl-1-pyrazolio)methyl-3-cephem-4-carboxylate trihydrochloride (5 kg) was dissolved in water (16 l). This solution was subjected to column chromatography on macroporous non-ionic adsorption resin "Diaion HP-20".

The desired product was eluted with water. To the eluate (30 l) was added acetone (160 l) and the mixture was stirred at room temperature for 2 hours. The resulting precipitate was collected by filtration to give 7β-amino-3-(3-amino-2-methyl-1-pyrazolio)methyl-3-cephem-4-carboxylate hydrochloride dihydrate as crystals (1.802 kg).

IR (Nujol): 3540, 3350, 3150, 1775, 1635, 1585 cm$^{-1}$

NMR (DMSO-d$_6$, δ): 3.66 (3H, s), 4.83 (1H, d, J=5Hz), 5.03 (1H, d, J=5Hz), 5.18 and 5.30 (2H, ABq, J=15Hz), 5.85(1H, d, J=3Hz), 7.44 (2H, broad s), 8.08 (1H, d, J=3Hz)

EXAMPLE 10

To N,N-dimethylformamide (231.6 ml) was added 7β-[2-(5-amino-1,2,4-thiadiazol-3-yl)-2-(1-carboxy-1-methylethoxyimino)acetamido]-3-(3-amino-2-methyl-1-pyrazolio)methyl-3-cephem-4-carboxylate (syn isomer) (38.6 g) at ambient temperature. The mixture was stirred at the same temperature for 2 hours, and the resultant precipitate was collected by filtration to give bis(N,N-dimethylformamide) solvate (47.3 g) of 7β-[2-(5-amino-1,2,4-thiadiazol-3-yl)-2-(1-carboxy-1-methylethoxyimino)acetamido]-3-(3-amino-2-methyl-1-pyrazolio)methyl-3-cephem-4-carboxylate (syn isomer).

IR (Nujol) : 3280, 3130, 1775, 1670, 1580 cm$^{-1}$

NMR (D$_2$O+NaHCO$_3$, δ) : 1.53 (6H, s), 2.86 (6H, s). 3.01 (6H, s), 3.10 and 3.36 (2H, ABq, J=18Hz), 3.66 (3H, s), 4.96 and 5.23 (2H, ABq, J=15Hz), 5.22 (1H, d, J=5Hz), 5.85 (1H, d, J=5Hz), 5.92 (1H, d, J=3Hz), 7.83 (1H, d, J=3Hz), 7.91 (2H, s)

EXAMPLE 11

To a solution of 7β-[2-(5-amino-1,2,4-thiadiazol-3-yl)-2-(1-carboxy-1-methylethoxyimino)acetamido]-3-(3-amino-2-methyl-1-pyrazolio)methyl-3-cephem-4-carboxylate (syn isomer) (0.5 g) in an aqueous sulfuric acid (2M, 1.0 ml) was added ethanol. After the solution was stirred for 1.0 hour, the crystals were collected by filtration, washed with a solution of water and ethanol (1:5), then washed with ethanol and dried over phosphorus pentoxide to give sulfuric acid salt (480 mg) of 7β-[2-(5-amino-1,2,4-thiadiazol-3-yl)-2-(1-carboxy-1-methylethoxyimino)acetamido]-3-(3-amino-2-methyl-1-pyrazolio)methyl-3-cephem-4-carb oxylate (syn isomer).

mp : 194–197° C.

IR (Nujol) : 3320, 3200, 3060, 1770, 1720, 1655, 1590, 1545 cm$^{-1}$

NMR (D$_2$O, δ) : 1.50 (6H, s), 3.33, 3.13 (2H, ABq, J=18Hz), 3.65 (3H, s), 5.20 (1H, d, J=5Hz), 5.22, 4.98 (2H, ABq, J=14Hz), 5.83 (1H, d, J=5Hz), 5.92 (1H, d, J=3Hz), 7.80 (1H, d, J=3Hz)

PREPARATION 17

To a solution of sulfuryl chloride (105.15 g) in methylene chloride (1500 ml) was added a solution of triphenyl phosphite (279 g) in methylene chloride (300 ml) at −20° C. and the mixture was stirred for 30 minutes at −20∼−30° C. To the mixture was added benzhydryl 7β-8-(2-hydroxybenzylideneamino)-3-hydroxyethyl-3-cephem-4-carboxylate (300 g) at −20∼−30° C. The mixture was stirred for 30 minutes at −20∼−30° C. and poured into a mixture of ethyl acetate (7.5 l) and 6.5% aqueous potassium carbonate (2.4 l). The organic layer was separated, washed with brine (300 ml) and concentrated in vacuo to 500 ml at 30° C. To the concentrated solution were added N,N-dimethylformamide (300 ml), 5-formamido-1-methylpyrazole (187.5 g) and potassium iodide (119.4 g) and the mixture was stirred for 22 hours at 31∼34° C. The reaction mixture was diluted with acetone (600 ml) and the dilute solution was added dropwise into the mixture of isopropyl alcohol (6.0 l) and diisopropyl ether (6.0 l)at 20∼25° C. The resulting precipitate was collected by filtration and dried in vacuo to give benzhydryl 7β-(2-hydroxy-benzylideneamino)-3-(3-formamido-2-methyl-1-pyrazolio)methyl-3-cephem-4-carboxylate iodide (514.8 g).

NMR (DMSO-d$_6$, δ) : 3.60 (2H, br s), 3.75 (3H, s), 5.50 (2H, br s), 5.33 (1H, d, J=6Hz), 5.90 (1H, d, J=6Hz), 6.60–7.60 (15H, m), 8.33–8.60 (3H, m), 8.90 (1H, s), 12.00 (1H, m)

IR (Nujol) : 1790, 1725, 1630, 1590, 1230, 1110 cm$^{-1}$

PREPARATION 18

To a solution of benzhydryl 7β-(2-hydroxybenzylideneamino)-3-(3-formamido-2-methyl-1-pyrazolio)methyl-3-cephem-4-carboxylate iodide (170 g) in methylene chloride and formic acid was added 35% hydrochloric acid (24.65 g). The mixture was stirred for 3 hours at 25∼30° C. and added dropwise into the mixture of acetone (1700 ml) and ethyl acetate (3400 ml). The resulting precipitate was collected by filtration and dried in vacuo to give 7β-amino-3-(3-formamido-2-methyl-1-pyrazolio)methyl-3-cephem-4-carboxylate hydrochloride (86.7 g).

IR (Nujol) : 1800, 1720, 1650, 1590 cm$^{-1}$

NMR (DMSO-d$_6$, δ) : 3.55 (2H, br s), 4.03 (3H, s), 5.30 (2H, br s), 5.33 (2H, br s), 6.80–7.60 (2H, m), 8.60 (1H, br s)

PREPARATION 19

To a solution of benzhydryl 7β-(2-hydroxybenzylideneamino)-3-(3-formamido-2-methyl-1-pyrazolio)methyl-3-cephem-4-carboxylate iodide (510 g) in methylene chloride (1275 ml) and formic acid (1275 ml) was added 35% hydrochloric acid (145 g) at 20∼25° C. The mixture was stirred for 1 hour at 20∼25° C. and added dropwise into the mixture of acetone (1020 ml) and ethyl acetate (2040 ml) at the same temperature. The resulting precipitate was collected by filtration and dried in vacuo to give the mixture (255.9 g) of 7βamino-3-(3-formamido-2-methyl-1-pyrazolio)methyl-3-cephem-4-carboxylate hydrochloride and 7β-amino-3-(3-amino-2-methyl-1-pyrazolio)methyl-3-cephem-4-carboxylate hydrochloride. The mixture (255.9 g) was dissolved in methanol (1023.6 ml). To the solution was added 35% hydrochloric acid (66.6 g) and the mixture was stirred for 1 hour at 28 ∼30° C. The insoluble material was filtered off and washed with methanol (512 ml). The combined filtrates and washings were added dropwise into the mixture of acetone (2560 ml) and ethyl acetate (5120 ml) at 20∼25° C. The resulting precipitate was collected by filtration and dried in vacuo to give 7β-amino-3-(3-amino-2-methyl-1-pyrazolio)methyl-3-cephem-4-carboxylate hydrochloride.

IR (Nujol) : 1800, 1720, 1650, 1600, 1230 cm$^{-1}$

NMR (DMSO-d$_6$, δ) : 3.30 and 3.55 (2H, ABq, J=18Hz), 3.70 (3H, s), 5.25 (2H, br s), 5.33 (2H, br s), 5.93 (1H, d, J=3Hz), 8.25 (1H, d, J=3Hz)

PREPARATION 20

A solution of sodium cyanate (52 g) in water (400 ml) was added dropwise to a solution of 1-methyl-5-aminopyrazole (19.4 g) in acetic acid (96 ml) and water (192 ml), and the mixture was stirred at ambient temperature for 7 hours. The reaction mixture was poured into a mixture of water (400 ml) and ethyl acetate (400 ml).

The organic layer was separated, washed with saturated aqueous sodium chloride, dried over magnesium sulfate and evaporated to give 1-methyl-5-ureidopyrazole (14.6 g).

IR (Nujol) 3300 (broad s), 1735, 1600 (broad s)cm$^{-1}$

NMR (DMSO-d$_6$, δ) : 3.63, 3.67 (3H, d, J=2Hz), 6.10, 6.22 (1H, dd, J=2Hz), 7.28, 7.35 (1H, d, J=2Hz).

PREPARATION 21

A mixture of acetic anhydride (11.13 ml) and formic acid (5.93 ml) was stirred at ambient temperature for 30 minutes. To this solution was added 5-amino-1-(2-hydroxyethyl)pyrazole (5 g) under ice-cooling, and the mixture was stirred at 30–40° C. for 1 hour. The reaction mixture was poured into a mixture of water, tetrahydrofuran and ethyl acetate and adjusted to pH 6 with aqueous sodium bicarbonate. The organic layer was separated, and the aqueous layer was extracted with a mixture of tetrahydrofuran and ethyl acetate for three times. The organic layers were combined, dried over magnesium sulfate and evaporated in vacuo to give 5-formamido-1-(2-formyloxyethyl)pyrazole (5.18 g).

IR (Nujol) : 3180, 1705, 1660 cm$^{-1}$

NMR (DMSO-d$_6$, δ) : 4.21–4.61 (4H, m), 6.11 and 6.34 (1H, each d, J=3Hz), 7.47 (1H, d, J=3Hz), 8.00 (1H, s), 8.33 (1H, s)

PREPARATION 22

The following compounds were obtained according to a similar manner to that of Preparation 3.

(1) Benzhydryl 7β-tert-butoxycarbonylamino-3-(3-acetamido-2-methyl-1-pyrazolio)methyl-3-cephem-4-carboxylate iodide IR (Nujol) : 1780, 1710 cm$^{-1}$ NMR (DMSO-d$_6$, δ) : 1.44 (9H, s), 2.25 (3H, s), 3.43 (2H, br s), 3.74 (3H, s), 5.16 (1H, d, J=5Hz), 5.38 (2H, br s), 5.63 (1H, dd, J=8, 5Hz), 6.93 (1H, d, J=3Hz), 6.94 (1H, s), 7.15–7.55 (10H, m), 7.97 (1H, d, J=8Hz), 8.25 (1H, d, J=3Hz), 11.13 (1H, s)

(2) Benzhydryl 7β-tert-butoxycarbonylamino-3-[3-formamido-2-(2-formyloxyethyl)-1-pyrazolio]methyl-3-cephem-4-carboxylate iodide IR (Nujol) : 1780, 1720 cm$^{-1}$ NMR (DMSO-d$_6$, δ) : 1.49 (9H, s), 3.43 (2H, br s), 4.14–4.38 (2H, m), 4.52–4.73 (2H, m), 5.15 (1H, d, J=5Hz), 5.40 (2H, br s), 5.67 (1H, dd, J=5, 8Hz), 6.88 (1H, s), 7.02 (1H, d, J=3Hz), 7.18–7.52 (10H, m), 7.94 (1H, d, J=8Hz), 7.99 (1H, s), 8.27 (1H, d, J=3Hz), 8.51 (1H, br s)

PREPARATION 23

The following compounds were obtained according to a similar manner to that of Preparation 5.

(1) Di(trifluoroacetic acid) salt of 7β-amino-3-[3-formamido-2-(2-formyloxyethyl)-1-pyrazolio]methyl-3-cephem-4-carboxylate IR (Nujol) : 1780, 1715, 1660 cm$^{-1}$ NMR (DMSO-d$_6$, δ) : 3.53 (2H, br s), 4.28–4.56 (2H, m), 4.78–4.99 (2H, m), 5.29 (2H, br s), 5.53 (2H, br s), 7.14 (1H, d, J=3Hz), 8.22 (1H, s), 8.46 (1H, d, J=3Hz), 8.63 (1H, s)

(2) Di(trifluoroacetic acid) salt of 7β-amino-3-(3-acetamido-2-methyl-1-pyrazolio)methyl-3-cephem-4-carboxylate IR (Nujol) : 1780, 1670 cm$^{-1}$ NMR (DMSO-d$_6$, δ) : 2.24 (3H, s), 3.47 (2H, br s), 3.93 (3H, s), 5.22 (2H, s), 5.50 (2H, br s), 6.98 (1H, d, J=3Hz), 8.35 (1H, d, J=3Hz)

PREPARATION 24

The following compound was obtained by reacting di(trifluoroacetic acid) salt of 7β-amino-3-[3-formamido-2-(2-formyloxyethyl)-1-pyrazolio]methyl-3-cephem-4-carboxylate according to a similar manner to that of Preparation 7.

7β-Amino-3-[3-amino-2-(2-hydroxyethyl)-1-pyrazolio]-methyl-3-cephem-4-carboxylate trihydrochloride IR (Nujol) : 3250, 1770, 1700, 1625 cm$^{-1}$ NMR (DMSO-d$_6$, δ) : 3.43 (2H, br s), 3.52–3.88 (2H, m), 4.18–4.48 (2H, m), 5.28 (2H, br s), 5.37 (2H, br s), 5.97 (1H, d, J=3Hz), 8.18 (1H, d, J=3Hz)

PREPARATION 25

To a solution of ammonium acetate (73.7 g) in methanol (250 ml) were added 2-(1-ethoxycarbonyl-1-methylethoxyimino)propanedinitrile (50.0 g) and 28% ammonia water (33.3 ml) at room temperature. After stirring for 15 hours at 20° C., potassium carbonate (33.0 g) was added to the solution, and the solution was evaporated under reduced pressure. A mixture of water (130 ml) and methylene chloride (110 ml) was added into the residue. The mixture was adjusted to pH 8.0–8.2 and extracted with methylene chloride twice. Phthalic acid (35.7 g) was added to the extract at 20–30° C., and then diisopropyl ether (200 ml) was added thereto. After stirring for 2 hours at the same temperature, the resulting precipitate was collected by filtration, washed with diisopropyl ether (40 ml) and dried under reduced pressure to give phthalic acid salt (61.4 g) of 2-cyano-2-(1-ethoxycarbonyl-1-methylethoxyimino)acetamidine.

mp : 156–158° C.

IR (Nujol) : 3380, 1730, 1700 cm$^{-1}$

NMR (DMSO-d$_6$, δ) : 1.20 (3H, t, J=7Hz), 1.66 (6H, s), 4.17 (2H, q, J=7Hz), 7.4–7.7 (2H, m), 7.9–8.2 (2H, m), 12.0 (5H, broad s)

PREPARATION 26

To a suspension of phthalic acid salt (10.0 g) of 2-cyano-2-(1-ethoxycarbonyl-1-methylethoxyimino)-acetamidine in methanol (60 ml) were added dropwise triethylamine (9.01 g) and bromine (3.67 g) at −15~−10° C. After stirring for 15 minutes at the same temperature, N,N-dimethylformamide (6.0 ml) and a solution of potassium thiocyanate (2.23 g) in methanol (22.3 ml) were added dropwise thereto at −15~−10° C. After stirring for one hour at −5~0° C., the solution was poured into cold water (300 ml) and the mixture was stirred for one hour under ice-cooling. The resulting precipitate was collected by filtration, washed with cold water (60 ml) and dried under reduced pressure to give 2-(5-amino-1,2,4-thiadiazol-3-yl)-2-(1-ethoxycarbonyl-1-methylethoxyimino)-acetonitrile (3.82 g).

IR (Nujol) : 3470, 3280, 3140, 1730, 1625, 1540 cm$^{-1}$

EXAMPLE 12

1-Methyl-5-ureidopyrazole (1.4 g) was added to a solution of 7β-[2-(5-amino-1,2,4-thiadiazol-3-yl)-2-(1-carboxy-1-methylethoxyimino)acetamido]-3-chloromethyl-3-cephem-4-carboxylic acid trifluoroacetate(syn isomer) (1.24 g) in N,N-dimethylformamide (13 ml) and the mixture was stirred at ambient temperature for 4 hours. The reaction mixture was poured into ethyl acetate (100 ml). The precipitates were collected by filtration and successively washed with ethyl acetate and diisopropyl ether, and the solid was dissolved in water (30 ml) and adjusted to pH 2.0 with 10% hydrochloric acid. The solution was subjected to column chromatography on macroporous non-ionic adsorption resin "Diaion HP-20" and eluted with 30% aqueous solution of methyl alcohol. The fractions containing the object compound were collected, concentrated in vacuo and lyophilized to give 7β-[2-(5-amino-1,2,4-thiadiazol-3-yl)-2-(1-carboxy-1-methylethoxyimino)acetamido]-3-(2-methyl-3-ureido-1-pyrazolio)methyl-3-cephem-4-carboxylate (syn isomer) (0.12 g).

IR (Nujol) : 3300 (broad s), 1770, 1680, 1570 cm$^{-1}$

NMR (D$_2$O, δ) : 1.53 (6H, s), 3.14, 3.44 (2H, ABq, J=18Hz), 3.70 (3H, s), 5.22 (1H, d, J=5Hz), 5.27 (2H, broad s), 5.85 (1H, d, J=5Hz), 6.75 (1H, d, J=3Hz), 8.10 (1H, d, J=3Hz)

EXAMPLE 13

The following compounds were obtained according to a similar manner to that of Example 12.

(1) 7β-[2-(5-Amino-1,2,4-thiadiazol-3-yl)-2-carboxymethoxyiminoacetamido]-3-(4-formamido-2-methyl-1-pyrazolio)methyl-3-cephem-4-carboxylate (syn isomer)

IR (Nujol) : 3300, 1765, 1665, 1605 cm$^{-1}$ (2) 7β-[2-(5-Amino-1,2,4-thiadiazol-3-yl)-2-carboxymethoxyiminoacetamido]-3-(3-formamido-2-methyl-1-pyrazolio)methyl-3-cephem-4-carboxylate (syn isomer)

IR (Nujol) : 3300, 1760, 1660, 1580 cm$^{-1}$ (3) 7β-[2-(5-Amino-1,2,4-thiadiazol-3-yl)-2-carboxymethoxyiminoacetamido]-3-(3-formamido-2,4-dimethyl-1-pyrazolio)methyl-3-cephem-4-carboxylate (syn isomer)

IR (Nujol) : 3300, 1765, 1660, 1600 cm$^{-1}$ (4) 7β-[2-(5-Amino-1,2,4-thiadiazol-3-yl)-2-carboxymethoxyiminoacetamido]-3-(3-amino-2-methyl-1-pyrazolio)methyl-3-cephem-4-carboxylate (syn isomer)

IR (Nujol) : 3300, 1760, 1660, 1590 cm$^{-1}$ (5) 7β-[2-(5-Amino-1,2,4-thiadiazol-3-yl)-2-carboxymethoxyiminoacetamido]-3-(3-amino-2,4-dimethyl-1-pyrazolio)methyl-3-cephem-4-carboxylate (syn isomer)

IR (Nujol) : 3350, 1770, 1660, 1600 cm$^{-1}$ (6) 7β-[2-(5-Amino-1,2,4-thiadiazol-3-yl)-2-(1-tert-butoxycarbonyl-1-methylethoxyimino)acetamido]-3-(3-amino-2-methyl-1-pyrazolio)methyl-3-cephem-4-carboxylate trihydrochloride (syn isomer)

IR (Nujol) : 3300, 1780, 1720, 1650 cm$^{-1}$ (7) 7β-[2-(5-Amino-1,2,4-thiadiazol-3-yl)-2-(1-tert-butoxycarbonyl-1-methylethoxyimino)acetamido]-3-(3-amino-2,4-dimethyl-1-pyrazolio)methyl-3-cephem-4-carboxylate trihydrochloride (syn isomer)

IR (Nujol) : 3300, 1780, 1650 cm$^{-1}$ (8) 7β-[2-(5-Amino-1,2,4-thiadiazol-3-yl)-2-(1-carboxy-1-methylethoxyimino)acetamido]-3-(3-amino-2-methyl-1-pyrazolio)methyl-3-cephem-4-carboxylate (syn isomer)

IR (Nujol) : 3325, 1770, 1650, 1630, 1590 cm$^{-1}$ (9) 7β-[2-(5-Amino-1,2,4-thiadiazol-3-yl)-2-1-carboxy-1-methylethoxyimino)acetamido]-3-(3-amino-2,4-dimethyl-1-pyrazolio)methyl-3-cephem-4-carboxylate (syn isomer)

IR (Nujol) : 3320, 3180, 1760, 1650, 1595 cm$^{-1}$

(10) 7β-[2-(5-Amino-1,2,4-thiadiazol-3-yl)-2-(1-carboxy-1-methylethoxyimino)acetamido]-3-(2-methyl-3-formamido-1-pyrazolio)methyl-3-cephem-4-carboxylate (syn isomer)

IR (Nujol) : 3200–3300, 1760, 1580 cm$^{-1}$

(11) 7β-[2-(5-Amino-1,2,4-thiadiazol-3-yl)-2-(1-carboxy-1-methylethoxyimino) acetamido]-3-[3-amino-2-(2-hydroxyethyl)-1-pyrazolio]methyl-3-cephem-4 1-carboxylate (syn isomer)

IR (Nujol) : 3300, 1765, 1640 cm$^{-1}$

(12) 7β-[2-(5-Amino-1,2,4-thiadiazol-3-yl)-2-(1-carboxy-1-methylethoxyimino)acetamido]-3-(3-acetamido-2-methyl-1-pyrazolio)methyl-3-cephem-4-carboxylate (syn isomer)

IR (Nujol) : 3300, 1775, 1670 cm$^{-1}$

What we claim is:

1. A compound of the formula:

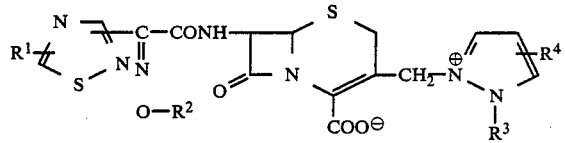

wherein R$^1$ and R$^4$ are each amino or a protected amino group,

R$^2$ is carboxy(lower)alkyl or esterifed carboxy(lower)alkyl, and

R$^3$ is hydroxy(lower)alkyl or a protected hydroxy(lower)alkyl, and a pharmaceutically acceptable salt thereof.

2. A compound of claim 1, wherein R$^3$ is hydroxy(lower)alkyl or lower alkanoyloxy(lower)alkyl.

3. A compound of claim 2, wherein R$^2$ is carboxy(lower)alkyl or lower alkoxycarbonyl(lower)alkyl.

4. A compound of claim 3, wherein R$^1$ is amino, R$^3$ is hydroxy(lower)alkyl, and R$^4$ is amino, 5. A compound of claim 7, wherein R$^2$ is carboxy(lower)alkyl or lower alkoxycarbonyl(lower)alkyl.

6. A compound of claim 5, wherein R$^1$ is amino, and R$^4$ is amino, lower alkanoylamino or ureido.

7. A compound of claim 1, wherein R$^2$ is 1-carboxy-1-methylethyl or carboxymethyl.

8. A pharmaceutical composition which comprises, as an active ingredient, a compound of claim 1 or a pharmaceutically acceptable salt thereof in admixture with pharmaceutically acceptable carriers.

9. A method for the treatment of infectious diseased which comprises administering a compound of claim 1 or a pharmaceutically acceptable salt thereof to human or animals.

* * * * *